United States Patent
Matsumoto et al.

(10) Patent No.: US 6,504,070 B2
(45) Date of Patent: Jan. 7, 2003

(54) METHOD OF ALKYLATING AROMATIC HYDROCARBON

(75) Inventors: Takaya Matsumoto, Yokohama (JP); Douglas Taube, Hayward, CA (US); Roy Anthony Periana, Los Altos, CA (US)

(73) Assignee: Nippon Mitsubishi Oil Corporation, Tokyo (JP)

( * ) Notice: Subject to any disclaimer, the term of this patent is extended or adjusted under 35 U.S.C. 154(b) by 0 days.

(21) Appl. No.: 09/775,697

(22) Filed: Feb. 2, 2001

(65) Prior Publication Data

US 2002/0052535 A1 May 2, 2002

(30) Foreign Application Priority Data

Feb. 3, 2000 (JP) .................................... 2000-032673

(51) Int. Cl.[7] .................................................. C07C 2/56
(52) U.S. Cl. ...................................... 585/457; 585/446
(58) Field of Search ............................... 583/457, 467, 583/446

(56) References Cited

U.S. PATENT DOCUMENTS

| | | | |
|---|---|---|---|
| 5,026,942 A | 6/1991 | Fellmann et al. | 585/467 |
| 5,866,736 A | 2/1999 | Chen | 585/323 |
| 6,033,643 A | 3/2000 | Yuen et al. | 423/718 |
| 6,111,157 A | 8/2000 | Hendriksen et al. | 585/467 |
| 6,153,806 A | 11/2000 | Gajda | 585/467 |

OTHER PUBLICATIONS

Cao, Y. et al. (1999). "Alkylation of Benzene with Dodecene. The Activity and Selectivity of Zeolite Type Catalysts as a Function of the Porous Structure" *Appl. Catal. A.* 184:231–238.

Bennett, M.A. and Mitchell, T.R.B. (1976). "γ–Carbon Bonded– 2,4–Pentanedionato Complexes of Trivalent Iridium," *Inorganic Chemistry* 15(11):2936–2938.

*Primary Examiner*—Thuan D. Dang
(74) *Attorney, Agent, or Firm*—Morrison & Foerster LLP

(57) ABSTRACT

A method of preparing an alkyl-substituted aromatic hydrocarbon, which comprises alkylating an aromatic hydrocarbon with an olefin in the presence of a catalyst comprising an iridium compound having at least one iridium atom and at least one β-diketonato ligand to produce the alkyl-substituted aromatic hydrocarbon.

17 Claims, No Drawings

METHOD OF ALKYLATING AROMATIC HYDROCARBON

This invention claims priority to Japanese Patent Application 2000-32673, filed Feb. 3, 2000.

BACKGROUND OF THE INVENTION

1. Field of the Invention

The present invention relates to a method of preparing an alkyl-substituted aromatic hydrocarbon, which comprises alkylating an aromatic hydrocarbon with an olefin in the presence of a catalyst comprising an iridium compound having at least one iridium atom and at least one β-diketonato ligand to produce the alkyl-substituted aromatic hydrocarbon.

2. Description of the Related Art

A method of preparing an alkylbenzene by using benzene and a straight-chain α-olefin has been known for a long time. However, since the alkylation is conducted at the β-position of the olefin in the Friedel-Crafts alkylation reaction using a Brønsted acid or a Lewis acid as the prior art, the main product is an alkylbenzene wherein the β-position is substituted with benzene. Depending on the reaction conditions, plural kinds of branched alkylbenzenes are further produced by the alkylation reaction between the branched olefin and the inner olefin produced by isomerization of the olefin, which occurs simultaneously. To produce a n-alkybenzene wherein the α-position is substituted with benzene, a combination of Friedel-Crafts acylation and a Clemmensen reduction must be employed. For example, n-propylbenzene must be obtained by acylating benzene with propanoyl chloride to form 1-phenyl-1-propanone and reducing said 1-phenyl-1-propanone, as shown in scheme (3) (see "BURGOYNE Organic Chemistry", written by E. E. BURGOYNE, translated by Toshio GOTO and Minoru ISOBE, (first edition and second impression), Mar. 1, 1984, published by Tokyo Kagaku Dojin, pages 98, 99, 141 and 142). A study of alkylation using the shape selectivity of zeolite has recently been reported (see, for example, Appl. Catal. A 184 (1999) 231–238, "Alkylation of benzene with dodecene. The activity and selectivity of zeolite type catalysts as a function of the porous structure", written by Y. Cao et al.). Even if n-alkylbenzene can be produced, it is difficult to selectively produce n-alkylbenzene by using these techniques.

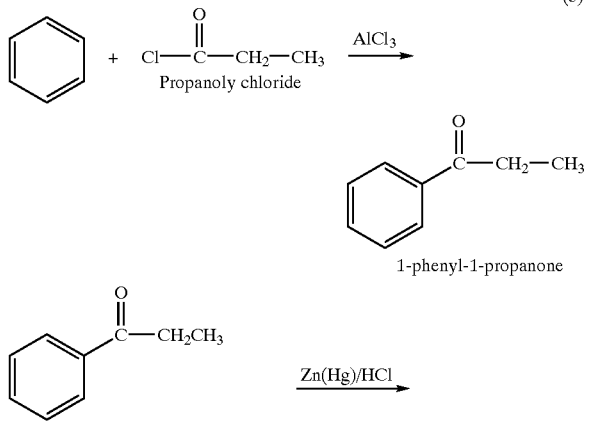

(3)

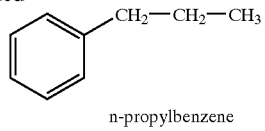

n-propylbenzene

As used herein, the term "selectively prepare" or "selectively produce" means that a desired aromatic hydrocarbon substituted with a desired alkyl and/or at a desired position is prepared or produced in a relatively higher proportion than that of the other substituted or non-substituted aromatic hydrocarbon or other products. Although its specific proportion varies depending on the compound to be substituted or substitution position (see Table 1), the relationship between the raw material and product can be clearly grasped by testing based on the matters disclosed in the present specification, particularly results of Examples and Table 1. Similarly, the term "high selectivity" means that a target alkyl-substituted aromatic hydrocarbon is produced in a higher proportion than that of the other reaction products (which are typically undesired products). Similarly, the term "mainly includes" means that the amount of the product is significantly larger than that of the other products.

The present invention makes it possible to efficiently prepare an aromatic hydrocarbon substituted with a predetermined alkyl at a predetermined position, which has never before been easily obtained by a conventional method, comparatively easily by using a specific catalyst.

The aromatic hydrocarbon obtained by the reaction can be optionally separated by a conventional method such as distillation to give a final product.

When 2,6-diethylnaphthalene is prepared by using naphthalene and ethylene, 1-alkylnaphthalene is selectively produced by the Friedel-Crafts alkylation reaction using a Brønsted acid or a Lewis acid as the prior art because of high orientation to the α-position of naphthalene. Furthermore, it is difficult to selectively produce 2,6-diethylnaphthalene because of the low position selectivity of the second alkylation and the occurrence of isomerization. An improvement in selectivity of 2,6-dipropylnaphthalene due to the shape selectivity of zeolite has recently been reported (U.S. Pat. No. 5,026,942), where high selectivity has been realized by using propylene as an olefin. If 2,6-naphthalenedicarboxylic acid is prepared from 2,6-dialkylnaphthalene, the smaller the number of the carbon atoms in the naphthalene side chain, the better.

If polyalkylation is conducted using benzene and an olefin, o- and p-dialkylbenzenes are selectively produced by the Friedel-Crafts alkylation reaction using a Brønsted acid or a Lewis acid as the prior art in accordance with o- and p-orientations, thus making it difficult to obtain a m-dialkylbenzene.

BRIEF SUMMARY OF THE INVENTION

The present invention relates to a method of preparing an alkyl-substituted aromatic hydrocarbon, which comprises alkylating an aromatic hydrocarbon with an olefin in the presence of a catalyst comprising an iridium compound having at least one iridium atom and at least one β-diketonato ligand to produce the alkyl-substituted aromatic hydrocarbon. The present invention relates to a method of preparing an alkyl-substituted aromatic hydrocarbon, which comprises using an iridium complex having a β-diketonato ligand as a catalyst in the case where an aromatic hydrocarbon is alkylated with an olefin, wherein said olefin is a substituted or non-substituted olefin having 2 to 20 carbon atoms (in which a substituent may be straight-chain or branched and also may contain one or more than one heteroatoms) and said aromatic hydrocarbon is a monocyclic or polycyclic aromatic hydrocarbon having 6 to 20 carbon atoms (said aromatic hydrocarbon may have a substituent and the substituent may contain a heteroatom or heteroatoms).

This present invention also relates to a method of preparing an alkyl-substituted aromatic hydrocarbon, in the presence of a catalyst wherein said iridium complex having a β-diketonato ligand is an iridium complex having a structure represented by the following formula (1).

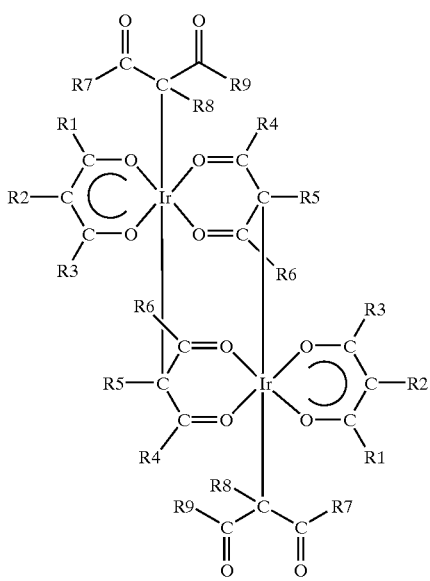

(1)

(provided that R1 to R9 respectively represent an arbitrary substituent and may be the same). More specifically, the present invention relates to a method of preparing an alkyl-substituted aromatic hydrocarbon by selectively bonding a terminal carbon of an olefin with an aromatic in case the aromatic hydrocarbon is alkylated with the olefin. A particularly useful reaction is a reaction of alkylating benzene with 1-dodecene or isobutene to obtain n-dodecylbenzene or isobutylbenzene, respectively. n-dodecylbenzene is a useful compound for use as a raw material of lubricating oils and detergents, while isobutylbenzene is a useful compound for use as a raw material for ibuprofen as a drug. Alternatively, there is a reaction of alkylating naphthalene with an ethylene to obtain 2,6-diethylnaphthalene. It is possible to obtain 2,6-naphthalenedicarboxylic acid as a useful raw polymer material by oxidizing 2,6-diethylnaphthalene. These alkyl-substituted aromatic hydrocarbons are useful compounds for use as raw materials of lubricating oils, detergents, drugs, pesticides, and polymers.

DETAILED DESCRIPTION OF THE INVENTION

An object of preferred embodiment of the present invention is to provide a novel method of synthesizing an alkyl-substituted aromatic hydrocarbon by alkylation in accordance with the anti-Markovnikov rule.

The present inventors have intensively studied methods of preparing an alkyl-substituted, particularly a straight-chain alkyl-substituted, aromatic hydrocarbons. As a result, they have found a technique of bonding an olefin and especially the terminal carbon of an olefin with an aromatic and, particularly, a method of alkylating by the addition of the anti-Markovnikov rule, by using an iridium complex having a β-diketonato ligand as a catalyst. The present invention will be described in detail below.

The Markovnikov rule was originally induced from the addition of a hydrogen halide to an olefin and refers to the case where a hydrogen atom of a substrate is bonded with a carbon atom having a larger number of hydrogen atoms bonded among double-bonded carbon atoms of the olefin (see aforecited "BURGOYNE Organic Chemistry", written by E. E. BURGOYNE, translated by Toshio GOTO and Minoru ISOBE, (first edition and second impression), Mar. 1, 1984, published by Tokyo Kagaku Dojin, pages 98, 99, 141 and 142). This rule is also applied to the Friedel-Crafts alkylation. If benzene is alkylated with isobutene as shown in scheme (4), tert-butylbenzene is obtained, as a product, as a result of the alkylation at the β-position of the olefin ("Morrison Boyd Organic Chemistry (the second)" (fifth edition), written by R. T. Morrison and R. N. Boyd, translated by Koji NAKANISHI et al., (fifth edition and fourth impression), Jun. 10, 1992, published by Tokyo Kagaku Dojin, page 696). It is the anti-Markovnikov rule which is antithetical to this Markovnikov rule, and the anti-Markovnikov rule refers to the case where a hydrogen atom is bonded with a carbon atom having a smaller number of hydrogen atoms on the olefin.

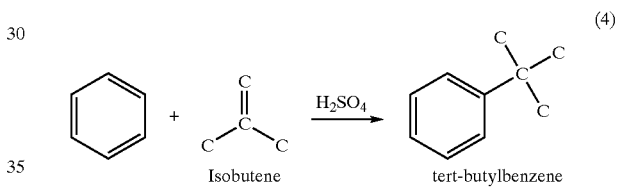

(4)

Isobutene          tert-butylbenzene

The aromatic hydrocarbon used in the present invention is a cyclic compound wherein a π electron orbital is delocalized, and any monocyclic and polycyclic compound can be used. Specifically, it is preferably an aromatic having 6 to 20 carbon atoms, and preferably 6 to 12 carbon atoms. At least one atom of the aromatic ring has hydrogen which is covalently bonded with the atom. Such an aromatic can contain a substituent. The substituent may be straight-chain, branched, or cyclic hydrocarbon. Examples of the substituent include, but are not limited to, an alkyl group, a cycloalkyl group, an aryl group, an alkaryl group, an aralkyl group and the like. Examples of the alkyl group include, but are not limited to, methyl group, ethyl group, isopropyl group, n-propyl group, isobutyl group, n-butyl group, sec-butyl group, tert-butyl group and the like. Examples of the cycloalkyl group include, but are not limited to, cyclopropyl group, cyclobutyl group, cyclopentyl group, cyclohexyl group and the like. Examples of the aryl group include, but are not limited to, a phenyl group, a naphthyl group and the like. Examples of the alkaryl group include, but are not limited to, 2-methylphenyl group (o-tolyl group), 3-methylphenyl group (m-tolyl group), 4-methylphenyl group (p-tolyl group), 2,3-dimethylphenyl group (2,3-xylyl group), 3,4-dimethylphenyl group (3,4-xylyl group), 2,4,6-trimethylxylyl group (mesityl group) and the like. Examples of the aralkyl group include, but are not limited to, phenylmethyl group (benzyl group), phenylethyl group (phenethyl group), triphenylmethyl group (trityl group) and the like.

The aromatic and substituent of the aromatic can further contain one or more than one non-hydrocarbon substituents having one or more atoms other than hydrogen and carbon. Examples of the non-hydrocarbon substituent include, but are not limited to, a halogen atom(s) (—F, —Cl, —Br, —I), hydroxyl group (—OH), alkoxy groups (—OR), carboxyl group (—COOH), ester groups (—COOR), aldehyde group (—CHO), acyl groups (—C(=O)R), amide group (—C(=O)NH$_2$), substituted amide groups (—C(=O)NHR), —C(=O)NR$_2$), amino group (—NH$_2$), substituted amino groups (—NHR, —NR$_2$), nitro group (—NO$_2$), nitroso group (—NO), cyano group (—CN), cyanate group (—OCN), isocyanate group (—NCO), thiocyanate group (—SCN), isothiocyanate group (—NCS), thiol group (—SH), thioether groups (—SR), sulfo group (—SO$_3$H), alkyl halide groups (—CF$_3$) and the like. Preferably, the aromatic and substituent of the aromatic are those which do not poison an iridium catalyst described below and/or do not induce an undesirable secondary reaction.

Specific examples of the monocyclic aromatic include, but are not limited to, benzene, methylbenzene (toluene), 1,2-dimethylbenzene (o-xylene), 1,3-dimethylbenzene (m-xylene), 1,4-dimethylbenzene (p-xylene), 1,3,5-trimethylbenzene (mesitylene), 1,2,3-trimethylbenzene, 1,2,4-trimethylbenzene, tetramethylbenzene, pentamethylbenzene, ethylbenzene, n-propylbenzene, isopropylbenzene (cumene), 1-isopropyl-4-methylbenzene (p-cymene), n-butylbenzene, 2-butylbenzene, isobutylbenzene, tert-butylbenzene, n-pentylbenzene, cyclopentylbenzene, neopentylbenzene, cyclohexylbenzene, 1-cyclohexyl-4-methylbenzene, cyclooctylbenzene and the like.

Specific examples of the polycyclic aromatic include, but are not limited to, biphenyl, biphenylene, terphenyl, naphthalene, azulene, anthracene, phenanthrene, triphenylene, pyrene, 1-methylnaphthalene, 2-methylnaphthalene, 1-ethylnaphthalene, 2-ethylnaphthalene, 2,2'-dimethylbiphenyl, diphenylethane, 1,2-diphenylethane, 1,8-diphenyloctane and the like.

Specific examples of the aromatic containing a heteroatom include, but are not limited to, methoxybenzene (anisole), ethoxybenzene, nitrobenzene, methyl benzoate, ethyl benzoate, isobutyl benzoate, diphenyl ether, cyclohexyl phenyl ether, benzonitrile, phenyl acetate, phenyl hexanoate, tolyl acetate, phenol, benzaldehyde, acetophenone, chlorobenzene, 2-chloroxylene, bromobenzene, trichlorobenzene, 1,4-dichlorobenzene, 1,2-dibromobenzene and the like.

Specific examples of more preferred aromatic are benzene, methylbenzene (toluene), ethylbenzene, naphthalene, 2-ethylnaphthalene, and chlorobenzene.

The olefin used in the present invention is a compound having at least one carbon-carbon double bond, and any straight-chain, branched and cyclic compound can be used. Specifically, it is preferably an olefin having 2 to 20 carbon atoms and, preferably, 2 to 12 carbon atoms. Such an olefin can contain a substituent. The substituent may be straight-chain, branched, or cyclic hydrocarbon. Examples of the substituent include, but are not limited to, alkyl group, cycloalkyl group, aryl group, alkaryl group, aralkyl group and the like. Examples of the alkyl group include, but are not limited to, methyl group, ethyl group, isopropyl group, n-propyl group, isobutyl group, n-butyl group, sec-butyl group, tert-butyl group and the like. Examples of the cycloalkyl group include, but are not limited to, cyclopropyl group, cyclobutyl group, cyclopentyl group, cyclohexyl group and the like. Examples of the aryl group include, but are not limited to, phenyl group, naphthyl group and the like. Examples of the alkaryl group include, but are not limited to, 2-methylphenyl group (o-tolyl group), 3-methylphenyl group (m-tolyl group), 4-methylphenyl group (p-tolyl group), 2,3-dimethylphenyl group (2,3-xylyl group), 3,4-dimethylphenyl group (3,4-xylyl group), 2,4,6-trimethylxylyl group (mesityl group) and the like. Examples of the aralkyl group include, but are not limited to, phenylmethyl group (benzyl group), phenylethyl group (phenethyl group), triphenylmethyl group (trityl group) and the like. Examples of the unsaturated hydrocarbon substituent include, but are not limited to, vinyl group, allyl group and the like.

The olefin and substituent of the olefin can further contain one or more than one non-hydrocarbon substituents having one or more atoms other than hydrogen and carbon. Examples of the non-hydrocarbon substituent include, but are not limited to, halogen atoms (—F, —Cl, —Br, —I), hydroxyl group (—OH), alkoxy groups (—OR), carboxyl group (—COOH), ester groups (—COOR), aldehyde group (—CHO), acyl groups (—C(=O)R), amide group (—C(=O)NH$_2$), substituted amide groups (—C(=O)NHR), —C(=O)NR$_2$), amino group (—NH$_2$), substituted amino groups (—NHR, —NR$_2$), nitro group (—NO$_2$), nitroso group (—NO), cyano group (—CN), cyanate group (—OCN), isocyanate group (—NCO), thiocyanate group (—SCN), isothiocyanate group (—NCS), thiol group (—SH), thioether groups (—SR), sulfo group (—SO$_3$H), alkyl halide groups (—CF$_3$) and the like. Preferably, the olefin and substituent of the olefin are those which do not poison an iridium catalyst described below and/or do not induce an undesirable secondary reaction.

Specific examples of the straight-chain monoolefin include, but are not limited to, ethylene, propylene, 1-butene, 2-butene, straight-chain pentene (e.g. 1-pentene, 2-pentene, etc.), straight-chain hexene (e.g. 1-hexene, 2-hexene, 3-hexene, etc.), straight-chain heptene (e.g. 1-heptene, etc.), straight-chain octene (e.g. 1-octene, etc.), straight-chain nonene (e.g. 1-nonene, etc.), straight-chain decene (e.g. 1-decene, etc.), straight-chain dodecene (e.g. 1-dodecene, etc.), and straight-chain eicosene (e.g. 1-eicosene, etc.).

Specific examples of the branched monoolefin include, but are not limited to, isobutene (2-methylpropylene), 2-methyl-1-butene, 3-methyl-1-butene, 2,3,3-trimethyl-1-butene, 2-methyl-2-butene and the like.

Specific examples of the cyclic monoolefin include, but are not limited to, cyclopentene, methylcyclopentene, cyclohexene, 1-methylcyclohexene, 3-methylcyclohexene, 1,2-dimethylcyclohexene, cyclooctene and the like.

Specific examples of the polyolefin include, but are not limited to, 1,2-butyadiene (methylallene), 1,3-butadiene (bivinyl), 1,3-pentadiene, 1,5-heptadiene, divinylbenzene, vinylcyclohexene, allylcyclohexene and the like.

Specific examples of the olefin containing one or more than one heteroatoms include, but are not limited to, vinyl chloride, vinyl fluoride, vinylidene chloride, allyl bromide, chlorostyrene, trichloroethylene, acrylic acid, crotonic acid, maleic acid, methyl maleate, p-vinylbenzoic acid, vinyl acetate, allyl propionate, propenyl acetate, ethylidene diacetate, methyl acrylate, methyl methacrylate and the like.

Specific examples of more preferred olefin are ethylene, propylene, 1-hexene, 1-dodecene, isobutene, and methyl acrylate.

The iridium complex having a β-diketonato ligand, which is used as the catalyst in the method of the present invention, is a complex having at least one iridium atom and at least one β-diketonato ligand.

The β-diketonato ligand used in the catalyst, which is used as the catalyst in the method of the present invention, can mainly take eight kinds of coordination forms as shown in formula (5) below. In the formula (5) below, (a) is an anionic ligand obtained by proton dissociation of an enol tautomer of β-diketone, and is bidentate coordinated via an oxygen atom. (b) is also obtained by proton dissociation of an enol tautomer of β-diketone, and is monodentate coordinated via an oxygen atom. (c) is obtained by proton dissociation of a keto tautomer of β-diketone, and is monodentate coordinated via a carbon atom. (d) is monodentate coordinated by carbon of methylene obtained by proton dissociation of a methyl group of β-diketone. (e) is also obtained by proton dissociation of a methyl group of β-diketone, and is $\eta^3$-allyl-coordinated. (f) causes bidentate coordination via an oxygen atom and bridging to the subsequent metal due to a carbon atom. (g) causes bridging to the subsequent metal via an oxygen atom. (h) causes no dissociation of a proton from β-diketone. Specifically, the number of carbon atoms of the β-diketonato ligand is preferably within a range from 5 to 50, and preferably from 5 to 15. Such a β-diketonato ligand can contain a substituent at the positions of R1 and R3, and can contain a hydrogen atom or substituent at the position of R2. R1, R2 and R3 may be the same or different from each other. The substituent may be straight-chain, branched, cyclic, saturated, or unsaturated. Examples of the substituent include, but are not limited to, an alkyl group, a cycloalkyl group, an aryl group, an alkaryl group, an aralkyl group and the like. Examples of the alkyl group include, but are not limited to, methyl group, ethyl group, isopropyl group, n-propyl group, isobutyl group, n-butyl group, sec-butyl group, tert-butyl group and the like. Examples of the cycloalkyl group include, but are not limited to, cyclopropyl group, cyclobutyl group, cyclopentyl group, cyclohexyl group and the like. Examples of the aryl group include, but are not limited to, a phenyl group, a naphthyl group and the like. Examples of the alkaryl group include, but are not limited to, 2-methylphenyl group (o-tolyl group), 3-methylphenyl group (m-tolyl group), 4-methylphenyl group (p-tolyl group), 2,3-dimethylphenyl group (2,3-xylyl group), 3,4-dimethylphenyl group (3,4-xylyl group), 2,4,6-trimethylxylyl group (mesityl group) and the like. Examples of the aralkyl group include, but are not limited to, phenylmethyl group (benzyl group), phenylethyl group (phenethyl group), triphenylmethyl group (trityl group) and the like. Examples of the unsaturated hydrocarbon substituent include, but are not limited to, vinyl group, allyl group and the like.

(5)

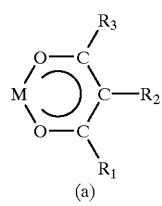

(a)

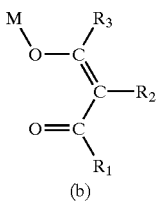

(b)

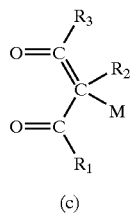

(c)

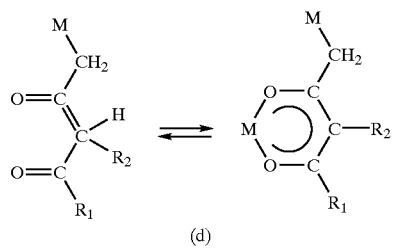

(d)

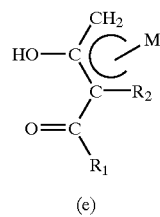

(e)

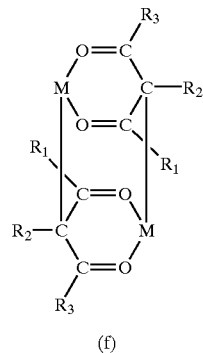

(f)

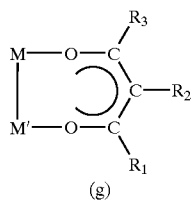

(g)

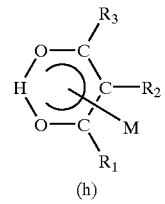

(h)

(provided that M and M' represent a metal, or a metal having an arbitrary ligand)

The β-diketonato ligand and substituent of the β-diketonato ligand can further contain one or more than one non-hydrocarbon substituents having one or more atoms other than hydrogen and carbon. Examples of the non-hydrocarbon substituent include, but are not limited to, one or more than one atoms (—F, —Cl, —Br, —I ), hydroxyl group (—OH), alkoxy groups (—OR), carboxyl group (—COOH), ester groups (—COOR), aldehyde group (—CHO), acyl groups (—C(=O)R), amide group (—C(=O)NH$_2$), substituted amide group (—C(=O)NHR), —C(=O)NR$_2$), amino group (—NH$_2$), substituted amino groups (—NHR, —NR$_2$), nitro group (—NO$_2$), nitroso group (—NO), cyano group (—CN), cyanate group (—OCN), isocyanate group (—NCO), thiocyanate group (—SCN), isothiocyanate group (—NCS), thiol group (—SH), thioether groups (—SR), sulfo group (—SO$_3$H), alkyl halide groups (—CF$_3$) and the like.

Specific examples of the β-diketonato ligand containing a substituent include, but are not limited to, 2,4-pentanedionato (acetylacetonato), 3-methyl-2,4-pentadionato, 2,4-hexanedionato, 2,2,6,6-tetramethyl-3,5-heptanedionato, 1,3-diphenyl-1,3-propanedionato and the like.

Specific examples of the β-diketonato ligand containing a heteroatom include, but are not limited to, 1,1,1-trifluoro-2,4-pentanedionato, 1,1,1,5,5,5-hexafluoro-2,4-pentanedionato (1,1,1,5,5,5-hexafluoroacetylacetonato), 1,1,1-trifluoro-2,4-hexanedionato, 1,1,1,2,2-pentafluoro-3,5-hexanedionato, 1,1,1,2,2,6,6,7,7,7-decafluoro-3,5-heptanedionato and the like.

Specific examples of more preferred β-diketonato ligand are 2,4-pentanedionato (acetylacetonato), 2,2,6,6-tetramethyl-3,5-heptanedionato, 1,3-diphenyl-1,3-propanedionato, 1,1,1-trifluoro-2,4-pentanedionato, and 1,1,1,5,5,5-hexafluoro-2,4-pentanedionato (hexafluoroacetylacetonato).

Specific example of a more preferred iridium complex having a β-diketonato ligand is bis(μ-2,4-pentanedionato-O,O',C$^3$) -bis(2,4-pentanedionato-O,O')-bis(2,4-pentanedionato-C$^3$)diiridium (III) having a structure represented by the following formula (6).

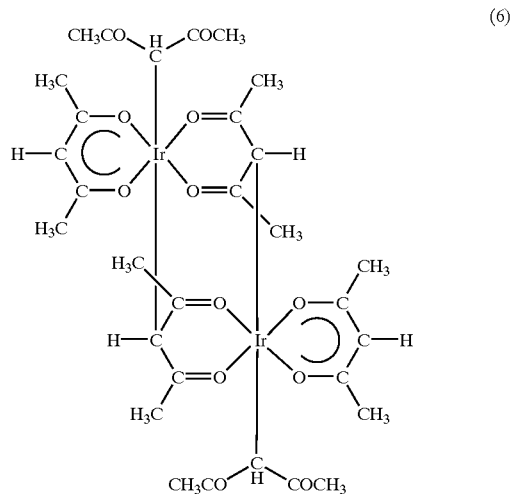

(6)

Although bis(μ-2,4-pentanedionato-O,O',C$^3$)-bis(2,4-pentanedionato-O,O')-bis(2,4-pentanedionato-C$^3$)diiridium (III) is an already-known compound (see "Inorg. Chem. Vol. 15, No. 11, 1976, 'γ-Carbon-Bonded 2,4-Pentanedionate Complexes of Trivalent Iridium'", pp 2936–2938), its catalytic action is not known. The present inventors have found, for the first time, that this compound functions as a catalyst capable of alkylating an aromatic hydrocarbon with an olefin.

The reaction can be accelerated by adding water or pentafluoropyridine, though the present invention does not require necessarily reaction accelerators. The reaction accelerator is a compound which has weak ability of coordination to iridium, so as not to inhibit the reaction site of the catalyst, and also has high polarity and is preferably water or pentafluoropyridine.

In case the aromatic hydrocarbon is liquid or the aromatic hydrocarbon and olefin are liquids in the present invention, the reaction medium may substantially be an aromatic hydrocarbon, or an aromatic hydrocarbon and an olefin. Therefore, solvents are not necessarily required, but may also be added. In case the aromatic hydrocarbon is solid (e.g. naphthalene, etc.), a solvent is required for dissolving the catalyst. The reaction can be conducted by using, as the solvent, a saturated hydrocarbon (e.g. n-heptane, 2,2,5,5-tetramethylhexane, etc.) or ether (e.g. ethylene glycol diethyl ether, etc.) which is inert to the reaction, or an aromatic hydrocarbon (e.g. 1,3,5-tri-tert-butylbenzene, etc.) which is inert to the reaction and is coated with a substituent causing large steric hindrance.

Where the method of the present invention is carried out, the reaction temperature is within a range from normal temperature to 300° C., and is preferably from 120 to 220° C.

The reaction pressure is within a range from atmospheric pressure to 30 MPa, and preferably from 0.5 to 5 MPa.

A molar ratio of the aromatic hydrocarbon as the reaction raw material to the iridium complex as the catalyst is not specifically limited, but is substantially within a range from 100000:1 to 10:1, and preferably from 10000:1 to 100:1.

The reaction can be conducted by any batch-wise, semibatch-wise and continuous method. The reaction is conducted in the batch-wise manner in the laboratory because of its simplicity, but it can be conducted in a continuous manner from an industrial point of view.

EXAMPLES

The following Examples further illustrate the present invention in detail, but the present invention is not limited by these Examples.

Example 1
Synthesis Reaction of Ethylbenzene

An [Ir(acac)$_3$]$_2$/benzene solution having the Ir concentration of 1 mM was prepared by dissolving 49.0 mg of bis(μ-2,4-pentanedionato-O,O',C$^3$)-bis(2,4-pentanedionato-O,O')-bis (2,4-pentanedionato-C$^3$)diiridium (III) (hereinafter referred to as (Ir(acac)$_3$)$_2$) in benzene saturated with water at room temperature to make 100 ml. 3 ml of the resulting solution and a stir bar coated with Teflon were introduced in a glass inner cylinder, which was then introduced in a stainless steel autoclave, After the atmosphere in the autoclave was purged by nitrogen, ethylene was injected up to 1.96 MPa at room temperature, followed by heating with stirring at. 180° C. for 20 minutes. After cooling, the liquid phase was analyzed by gas chromatography. The results are shown in Table 1.

Comparative Example 1

The reaction was conducted by the very same operation as in Example 1, except that 8.6 mg of 12 tungsto(VI) phosphoric acid (hereinafter referred to as H$_3$PW$_{12}$O$_{40}$) as the catalyst and 3 ml of benzene saturated with water at room temperature were introduced in the glass inner cylinder in place of the [Ir(acac)$_3$]$_2$)/benzene solution. The results are shown in Table 1.

Example 2
Synthesis Reaction of Propylbenzene

The reaction was conducted by the very same operation as in Example 1, except that propylene was injected up to 0.78 MPa at room temperature in place of ethylene and nitrogen was subsequently injected up to 1.96 MPa. The results are shown in Table 1.

Comparative Example 2

The reaction was conducted by the very same operation as in Comparative Example 1, except that propylene was injected up to 0.78 MPa at room temperature in place of ethylene and nitrogen was subsequently injected up to 1.96 MPa. The results are shown in Table 1.

Example 3
Synthesis Reaction of Butylbenzene

The reaction was conducted by the very same operation as in Example 1, except that isobutene was injected up to 0.20 MPa at room temperature in place of ethylene and nitrogen was subsequently injected up to 1.96 MPa and that heating was conducted with stirring for two hours in place of heating with stirring for 20 minutes. The results are shown in Table 1.

Comparative Example 3

The reaction was conducted by the very same operation as in Comparative Example 1, except that isobutene was injected up to 0.20 MPa at room temperature in place of ethylene and nitrogen was subsequently injected up to 1.96 MPa. The results are shown in Table 1.

Example 4
Synthesis Reaction of Hexylbenzene

A benzene/1-hexene mixed solution having the benzene concentration of 8.8 M was prepared from benzene saturated with water and 1-hexene. An $(Ir(acac)_3)_2$/benzene/1-hexene solution having the Ir concentration of 1 mM was prepared by dissolving 49.0 mg of $(Ir(acac)_3)_2$) in the resulting solution to make 100 ml. 3 ml of the resulting solution and a stir bar coated with Teflon were introduced in a glass inner cylinder, which was then introduced in a stainless steel autoclave. After the atmosphere in the autoclave was purged by nitrogen, nitrogen was injected up to 2.94 MPa at room temperature, followed by heating with stirring at 180° C. for 20 minutes After cooling, the liquid phase was analyzed by gas chromatography. The results are shown in Table 1.

Comparative Example 4

The reaction was conducted by the very same operation as in Example 4, except that 8.6 mg of the catalyst $H_3PW_{12}O_{40}$ and 3 ml of a benzene/1-hexene mixed solution having the benzene concentration of 8.8 M prepared from benzene saturated with water at room temperature and 1-hexene were introduced in the glass inner cylinder in place of the $[Ir(acac)_3]_2$/benzene/1-hexene solution. The results are shown in Table 1.

Example 5
Synthesis Reaction of Dodecylbenzene

The reaction was conducted by the very same operation as in Example 4, except that a benzene/1-dodecene mixed solution having the benzene concentration of 7.6 m prepared from benzene saturated with water at room temperature and 1-dodecene was used in place of the benzene/1-hexene mixed solution, having a benzene concentration of 8.8 M, prepared from benzene saturated with water at room temperature and 1-hexene. The results are shown in Table 1.

Comparative Example 5

The reaction was conducted by the very same operation as in Comparative Example 4, except that a benzene/1-dodecene mixed solution having the benzene concentration of 7.6 M prepared from benzene saturated with water at room temperature and 1-dodecene was used in place of the benzene/1-hexene mixed solution having the benzene concentration of 8.8 M prepared from benzene saturated with water at room temperature and 1-hexene. The results are shown in Table 1.

Example 6
Synthesis Reaction of Ethylnaphthalene

An $(Ir(acac)_3)_2$/naphthalene/n-heptane solution having the Ir concentration of 1 mM was prepared by dissolving 49.0 mg of $[Ir(acac)_3]_2$) in a naphthalene/n-heptane mixed solution having the naphthalene concentration of 0.5 M to make 100 ml. 3 ml of the resulting solution, 10 mg of water and a stir bar coated with Teflon were introduced in a glass inner cylinder, which was then introduced in a stainless steel autoclave. After the atmosphere in the autoclave was purged by nitrogen, ethylene was injected up to 1.96 MPa at room temperature, followed by heating with stirring at 180° C. for 2 hours. After cooling, the liquid phase was analyzed by gas chromatography. The results are shown in Table 1.

Comparative Example 6

The reaction was conducted by the very same operation as in Example 6, except that 8.6 mg of the catalyst $H_3PW_{12}O_{40}$ and 3 ml of a naphthalene/n-heptane mixed solution having the naphthalene concentration of 0.5 M were introduced in the glass inner cylinder in place of the $(Ir(acac)_3)_2$/naphthalene/n-heptane solution. The results are shown in Table 1.

Example 7
Synthesis Reaction of Diethylnaphthalene

The reaction was conducted by the very same operation as in Example 1, except that 2-ethylnaphthalene saturated with water at room temperature was used in place of benzene saturated with water at room temperature. The results are shown in Table 1.

Comparative Example 7

The reaction was conducted by the very same operation as in Comparative Example 1, except that 2-ethylnaphthalene saturated with water at room temperature was used in place of benzene saturated with water at room temperature. The results are shown in Table 1.

Example 8
Synthesis Reaction of Diethylbenzene

The reaction was conducted by the very same operation as in Example 1, except that ethylbenzene saturated with water at room temperature was used in place of benzene saturated with water at room temperature. The results are shown in Table 1.

Comparative Example 8

The reaction was conducted by the very same operation as in Comparative Example 1, except that ethylbenzene saturated with water at room temperature was used in place of benzene saturated with water at room temperature. The results are shown in Table 1.

Example 9
Synthesis Reaction of Ethylmethylbenzene

The reaction was conducted by the very same operation as in Example 1, except that toluene saturated with water at room temperature was used in place of benzene saturated with water at room temperature. The results are shown in Table 1.

Example 10
Synthesis Reaction of Chloroethylbenzene

The reaction was conducted by the very same operation as in Example 1, except that chlorobenzene saturated with water at room temperature was used in place of benzene saturated with water at room temperature. The results are shown in Table 1.

Example 11

Synthesis Reaction of Methyl 3-phenylpropionic Acid Methyl Ester

The reaction was conducted by the very same operation as in Example 4, except that a benzene/methyl acrylate mixed solution having the benzene concentration of 10.1 M prepared from benzene saturated with water at room temperature and methyl acrylate was used in place of the benzene/1-hexene mixed solution having the benzene concentration of 8.8 M prepared from benzene saturated with water at room temperature and 1-hexene. The results are shown in Table 1.

TABLE 1

The results of alkylation reaction of various aromatics due to various olefins

| | Olefins | Aromatics | Catalysts | Molar concentration of product (mM) | TOF ($\times 10^{-4} s^{-1}$) | Selectivities in mono-substituted compound | |
|---|---|---|---|---|---|---|---|
| | | | | | | Name | Mole (%) |
| Example 1 | Ethylene | Benzene | $(Ir(acac)_3)_2$ | 50.2 | 418.0 | Ethylbenzene | |
| Comp. Example 1 | Ethylene | Benzene | $H_3PW_{12}O_{40}$ | 10.5 | 87.3 | Ethylbenzene | |
| Example 2 | Propylene | Benzene | $(Ir(acac)_3)_2$ | 13.3 | 110.7 | n-propylbenzene | 61 |
| | | | | | | Cumene | 39 |
| Comp. Example 2 | Propylene | Benzene | $H_3PW_{12}O_{40}$ | 578.6 | 4821.5 | n-propylbenzene | 0 |
| | | | | | | Cumene | 100 |
| Example 3 | Isobutene | Benzene | $(Ir(acac)_3)_2$ | 2.2 | 3.0 | Isobutylbenzene | 82 |
| | | | | | | tert-butylbenzene | 18 |
| Comp. Example 3 | Isobutene | Benzene | $H_3PW_{12}O_{40}$ | 63.6 | 529.8 | Isobutylbenzene | 0 |
| | | | | | | tert-butylbenzene | 100 |
| Example 4 | 1-hexene | Benzene | $(Ir(acac)_3)_2$ | 8.3 | 69.0 | 1-phenylhexane | 69 |
| | | | | | | 2-phenylhexane | 31 |
| | | | | | | 3-phenylhexane | 0 |
| Comp. Example 4 | 1-hexene | Benzene | $H_3PW_{12}O_{40}$ | 108.7 | 905.4 | 1-phenylhexane | 0 |
| | | | | | | 2-phenylhexane | 66 |
| | | | | | | 3-phenylhexane | 34 |
| Example 5 | 1-dodecene | Benzene | $(Ir(acac)_3)_2$ | 5.4 | 44.8 | 1-phenyldodecane | 69 |
| | | | | | | 2-phenyldodecane | 31 |
| | | | | | | Other phenyldecane isomer | 0 |
| Comp. Example 5 | 1-dodecene | Benzene | $H_3PW_{12}O_{40}$ | 33.2 | 276.7 | 1-phenyldodecane | 0 |
| | | | | | | 2-phenyldodecane | 64 |
| | | | | | | Other phenyldecane isomer | 36 |
| Example 6 | Ethylene | Naphthalene | $(Ir(acac)_3)_2$ | 1.6 | 2.2 | 2-ethylnaphthalene | 100 |
| | | | | | | 1-ethylnaphthalene | 0 |
| Comp. Example 6 | Ethylene | Naphthalene | $H_3PW_{12}O_{40}$ | 25.1 | 34.9 | 2-ethylnaphthalene | 29 |
| | | | | | | 1-ethylnaphthalene | 71 |
| Example 7 | Ethylene | 2-ethylnaphthalene | $(Ir(acac)_3)_2$ | 29.6 | 246.3 | 2,6-diethylnaphthalene | 45 |
| | | | | | | 2,7-diethylnaphthalene | 45 |
| | | | | | | Isomers other than 2,6- and 2,7-isomers | 9 |
| Comp. Example 7 | Ethylene | 2-ethylnaphthalene | $H_3PW_{12}O_{40}$ | 34.2 | 284.9 | 2,6-diethylnaphthalene | 7 |
| | | | | | | 2,7-diethylnaphthalene | 34 |
| | | | | | | Isomers other than 2,6- and 2,7-isomers | 59 |
| Example 8 | Ethylene | Ethylbenzene | $(Ir(acac)_3)_2$ | 25.7 | 214.3 | p-diethylbenzene | 30 |
| | | | | | | m-diethylbenzene | 70 |
| | | | | | | o-diethylbenzene | 0 |
| Comp. Example 8 | Ethylene | Ethylbenzene | $H_3PW_{12}O_{40}$ | 6.7 | 56.2 | p-diethylbenzene | 29 |
| | | | | | | m-diethylbenzene | 32 |
| | | | | | | o-diethylbenzene | 39 |
| Example 9 | Ethylene | Toluene | $(Ir(acac)_3)_2$ | 22.3 | 185.5 | p-methylethylbenzene | 37 |
| | | | | | | m-methylethylbenzene | 63 |
| | | | | | | o-methylethylbenzene | 0 |
| Example 10 | Ethylene | Chlorobenzene | $(Ir(acac)_3)_2$ | 12.5 | 104.5 | p-chloroethylbenzene | 33 |
| | | | | | | m-chloroethylbenzene | 67 |
| | | | | | | o-chloroethylbenzene | 0 |
| Example 11 | Methyl acrylate | Benzene | $(Ir(acac)_3)_2$ | 4.7 | 38.9 | 3-phenylpropionic acid methyl ester | 68 |
| | | | | | | 2-phenylpropionic acid methyl ester | 32 |

As is apparent from Table 1, no n-alkylbenzene is produced in case of heteropolyacid $H_3PW_{12}O_{40}$ as a typical Brønsted acid, whereas, n-alkylbenzene is selectively produced in the case of an $(Ir(acac)_3)_2$ complex catalyst. The selectivity of 2-ethylnaphthalene and 2,6-diethylnaphthalane is low in the case of heteropolyacid, whereas, the selectivity of 2-ethylnaphthalene and 2,6-diethylnaphthalane is high in the case of an $(Ir(acac)_3)_2$ complex catalyst. Furthermore, the selectivity of m-diethylbenzene is low in the case of $H_3PW_{12}O_{40}$, whereas, the selectivity of m-diethylbenzene is high in the case of an $(Ir(acac)_3)_2$ complex catalyst. In this table, mM (millimolar) is a molar concentration of the product in the reaction solution. TOF (turn over frequency) was defined as follows.

TOF=((mole number of product)/(mole number of catalyst))/reaction time (second)

Example 12
Synthesis Reaction of Ethylbenzene

The reaction was conducted by the very same operation as in Example 1, except that the heating was conducted with stirring at 200° C. in place of heating with stirring at 180° C. The results are shown in Table 2.

Example 13

The reaction was conducted by the very same operation as in Example 1, except that the 10 mg of pentafluoropyridine was added to 3 ml of the $(Ir(acac)_3)_2$/benzene solution prepared by using distilled benzene in place of benzene saturated with water at room temperature. The results are shown in Table 2.

Comparative Example 9

The reaction was conducted by the very same operation as in Example 1, except that distilled benzene was used in place of benzene saturated with water at room temperature. The results are shown in Table 2.

preparation of a straight-chain alkyl-substituted aromatic hydrocarbon such as n-alkylbenzene, or 2-alkylnaphthalene, 2,6-dialkylnaphthalene, or m-dialkylbenzene, at a high selectivity.

What is claimed is:

1. A method of preparing an alkyl-substituted aromatic hydrocarbon, which comprises alkylating an aromatic hydrocarbon with an olefin in the presence of a catalyst comprising an iridium compound having at least one iridium atom and at least one β-diketonato ligand to produce the alkyl-substituted aromatic hydrocarbon.

2. A method according to claim 1, wherein said olefin has from 2 to 20 carbon atoms and said aromatic hydrocarbon is a monocyclic or polycyclic aromatic hydrocarbon having from 6 to 20 carbon atoms.

3. A method according to claim 2, wherein said olefin is unsubstituted.

4. A method according to claim 2, wherein said olefin is substituted with a straight-chain or branched hydrocarbon.

5. A method according to claim 4, wherein said straight-chain or branched hydrocarbon contains one or more than one heteroatoms.

6. A method according to claim 2, wherein said aromatic hydrocarbon is unsubstituted.

7. A method according to claim 2, wherein said aromatic hydrocarbon is substituted with a straight-chain or branched hydrocarbon.

8. A method according to claim 7, wherein said straight-chain or branched hydrocarbon contains one or more than one heteroatoms.

9. A method according to claim 1, wherein a major portion of said alkyl-substituted aromatic hydrocarbon is a straight-chain alkyl-substituted aromatic hydrocarbon.

10. A method according to claim 1, wherein a major portion of said alkyl-substituted aromatic hydrocarbon is a m-dialkylbenzene.

TABLE 2

The addition effect of reaction accelerator in alkylation reaction between ethylene and benzene

|  | Solvents | Catalysts | (Ethylbenzene) (mM) | TOF ($\times 10^{-4} s^{-1}$) |
|---|---|---|---|---|
| Example 12 | Water-saturated benzene | $(Ir(acac)_3)_2$ | 156.6 | 1304.2 |
| Example 13 | Benzene/pentafluoropyridine | $(Ir(acac)_3)_2$ | 132.2 | 1102.0 |
| Comp. Example 9 | Distilled benzene | $(Ir(acac)_3)_2$ | 58.6 | 488.6 |

As is apparent from Table 2, water or pentafluoropyridine functions as a reaction accelerator.

According to the present invention, it is made possible to attain a technique of bonding a terminal carbon of an olefin with an aromatic hydrocarbon, which has been considered to be difficult to attain, i.e. a catalytic alkylation reaction in accordance with the anti-Markovnikov rule of an aromatic and an olefin. This technique makes it possible to attain the 11. A method according to claim 1, wherein a major portion of said alkyl-substituted aromatic hydrocarbon is a member of the group consisting of 2-alkylnaphthalene and 2,6-dialkylnaphthalene.

12. A method according to claim 1, wherein said iridium compound comprises a structure represented by the following formula:

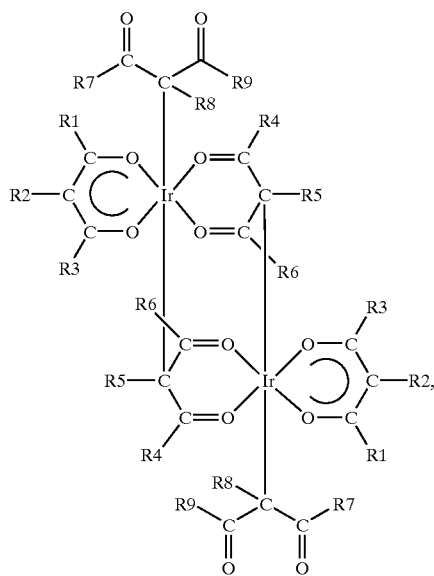

(1)

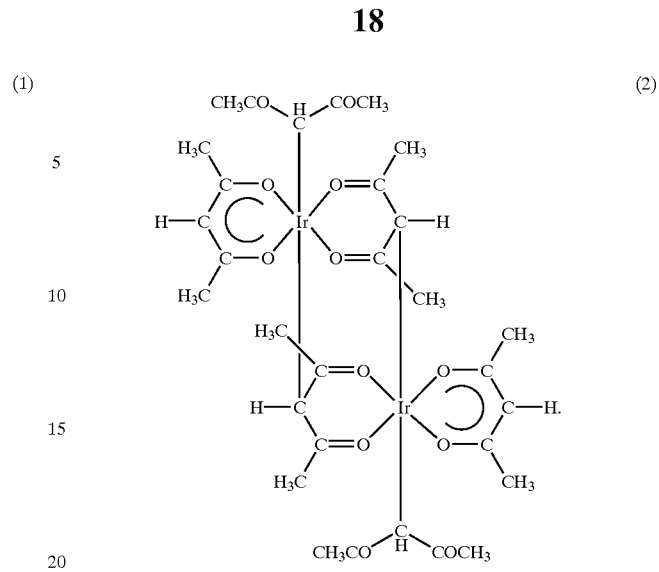

(2)

wherein each of R1 to R9 is individually a substituent that does not render the iridium compound ineffective to alkylate the aromatic hydrocarbon.

13. A method according to claim 12, wherein at least one of said R1 to R9 is a different substituent from another of said R1 to R9.

14. A method according to claim 12, wherein said iridium compound comprises a structure represented by the following formula:

15. A method according to claim 1, wherein said olefin is selected from the group consisting of ethylene, propylene, isobutene, 1-hexene, 1-dodecene, and methyl acrylate, and wherein said aromatic hydrocarbon is selected from the group consisting of benzene, ethylbenzene, toluene, chlorobenzene, naphthalene, and 2-ethylnaphthalene.

16. A method according to claim 1 and further comprising adding a reaction accelerator which has a sufficiently low coordinate bonding force to iridium so as not to inhibit said alkylating and which increases the rate of said alkylating.

17. A method according to claim 16 wherein the reaction accelerator comprises water or pentafluoropyridine to accelerate said alkylating.

* * * * *